(12) United States Patent
Kim et al.

(10) Patent No.: US 10,470,747 B2
(45) Date of Patent: Nov. 12, 2019

(54) ULTRASONIC IMAGING APPARATUS AND METHOD FOR CONTROLLING THE SAME

(71) Applicant: SAMSUNG MEDISON CO., LTD., Gangwon-do (KR)

(72) Inventors: Chan Mo Kim, Seoul (KR); Dae Young Kim, Seoul (KR); Tae-Heon Roh, Gwangmyeong-si (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 568 days.

(21) Appl. No.: 14/841,082

(22) Filed: Aug. 31, 2015

(65) Prior Publication Data

US 2016/0199040 A1 Jul. 14, 2016

(30) Foreign Application Priority Data

Jan. 13, 2015 (KR) .................. 10-2015-0006085

(51) Int. Cl.
*A61B 8/00* (2006.01)
*B06B 1/02* (2006.01)
*B06B 1/06* (2006.01)

(52) U.S. Cl.
CPC .............. *A61B 8/56* (2013.01); *A61B 8/4494* (2013.01); *A61B 8/467* (2013.01); *B06B 1/0215* (2013.01); *B06B 1/0292* (2013.01); *B06B 1/067* (2013.01); *A61B 2560/0214* (2013.01)

(58) Field of Classification Search
CPC ......................................... A61B 8/56
See application file for complete search history.

(56) References Cited

U.S. PATENT DOCUMENTS

2007/0016021 A1   1/2007  Moritz
2012/0314534 A1* 12/2012  Yoda .................. G01N 21/1702
                                                        367/7
2013/0116679 A1*  5/2013  Van der Weide ..........................
                                                        A61B 18/1815
                                                        606/33

* cited by examiner

*Primary Examiner* — Rochelle D Turchen
(74) *Attorney, Agent, or Firm* — Morgan, Lewis & Bockius LLP

(57) ABSTRACT

An ultrasonic imaging apparatus and a method for controlling the same are disclosed. The ultrasonic imaging apparatus includes: a user interface to receive an input signal of a user and a power-supply unit. The power-supply unit includes a plurality of power-supply groups to provide power-supply signals for respectively driving a plurality of elements, and a power-supply processor to search for power data corresponding to the received input signal from among predetermined power data and to adjust power-supply signals applied to respective elements corresponding to the plurality of power-supply groups according to the searched power data.

11 Claims, 8 Drawing Sheets

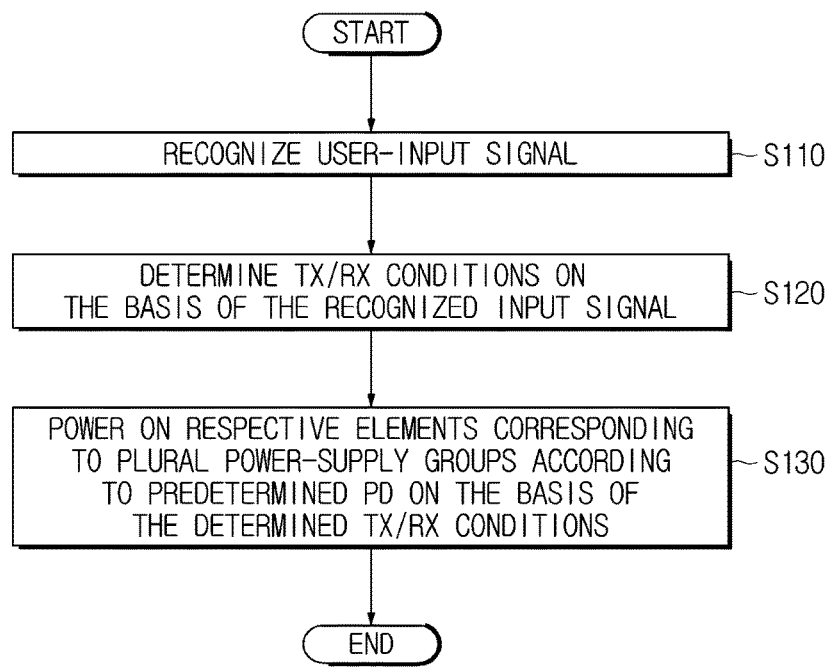

ULTRASONIC IMAGING APPARATUS AND METHOD FOR CONTROLLING THE SAME

CROSS-REFERENCE TO RELATED APPLICATION

This application claims priority to and the benefit of Korean Patent Application No. 10-2015-0006085, filed on Jan. 13, 2015 in the Korean Intellectual Property Office, the disclosure of which is incorporated herein by reference.

BACKGROUND

1. Field

Embodiments of the present invention relate to an ultrasonic imaging apparatus for controlling a power-supply voltage applied to a plurality of elements contained in an ultrasonic imaging apparatus, and a method for controlling the same.

2. Description of the Related Art

An ultrasonic imaging apparatus applies an ultrasonic signal from the surface of an object (for example, a human body) to a target site of the inside of the body of the object, and non-invasively acquires tomograms of soft tissues or images regarding blood flow using information of reflected ultrasonic signals (reflected ultrasonic echo signals). The ultrasonic imaging apparatus displays a diagnostic image in real time, and has compact size and low price, as compared to other imaging apparatuses, for example, an X-ray probe, an X-ray computed tomography (CT) scanner, a magnetic resonance imaging (MRI) apparatus, and a nuclear medical probe. In addition, since the ultrasonic imaging apparatus does not cause radiation exposure, the ultrasonic imaging apparatus is inherently safe. Accordingly, the ultrasonic imaging apparatus has been widely utilized for cardiac, abdominal, and urological diagnosis as well as obstetric and gynecological diagnosis.

Power consumption of the ultrasonic imaging apparatus continuously increases in proportion to increasing performance, such that many developers and companies are conducting intensive research into technology for efficiently managing a power-supply voltage applied to a plurality of elements contained in the ultrasonic imaging apparatus. In addition, since the ultrasonic imaging apparatus has been miniaturized or implemented as a mobile system, the necessity of driving the ultrasonic imaging apparatus using a small amount of power is increased, and efficient power management is of increasing importance.

SUMMARY

Therefore, it is an aspect of the present invention to provide an ultrasonic imaging apparatus and a method for controlling the same, which allow a plurality of power-supply groups to adjust power-supply voltages respectively applied to a plurality of elements in response to a user input signal.

Additional aspects of the invention will be set forth in part in the description which follows and, in part, will be obvious from the description, or may be learned by practice of the invention.

In accordance with one aspect of the present invention, an ultrasonic imaging apparatus includes: a user interface configured to receive an input signal of a user; and a power-supply unit including a plurality of power-supply groups to provide power-supply signals for respectively driving a plurality of elements, and a power-supply processor to search for power data corresponding to the received input signal from among predetermined power data and to adjust power-supply signals applied to respective elements corresponding to the plurality of power-supply groups according to the searched power data.

The power-supply processor may adjust the magnitude of power-supply signals applied to the plurality of elements.

The power-supply processor may turn on or off the plurality of power-supply groups so as to adjust power supply.

The input signal may be an operation mode of the ultrasonic imaging apparatus; and the power-supply processor may search for power data corresponding to the input operation mode, and adjust supply time points of power-supply signals applied to the plurality of elements according to the searched power data.

The power-supply processor may adjust the order of power-supply signals applied to the plurality of elements according to the searched power data.

The input signal may indicate transmission/reception (Tx/Rx) conditions regarding a frequency and interval of ultrasonic waves to be transmitted and received; and the power-supply processor may search for power data corresponding to the input transmission/reception (Tx/Rx) conditions, and adjust a switching frequency of power-supply signals applied to the plurality of elements according to the searched power data.

The power-supply groups may include different regulators.

The power-supply processor may adjust the switching frequency and supply time point of power-supply signals applied to the plurality of elements according to the searched power data.

The plurality of power-supply groups may be coupled in parallel according to the same-magnitude voltages.

In accordance with another aspect of the present invention, a method for controlling an ultrasonic imaging apparatus includes: receiving an input signal of a user; searching for power data corresponding to the received input signal from among predetermined power data; and adjusting power-supply signals applied to respective elements corresponding to a plurality of power-supply groups according to the searched power data.

BRIEF DESCRIPTION OF THE DRAWINGS

These and/or other aspects of the invention will become apparent and more readily appreciated from the following description of the embodiments, taken in conjunction with the accompanying drawings of which:

FIG. 8 is a flowchart illustrating a method for allowing a power-supply unit to provide a plurality of elements with power-supply voltages according to another embodiment.

DETAILED DESCRIPTION

Figure 1:
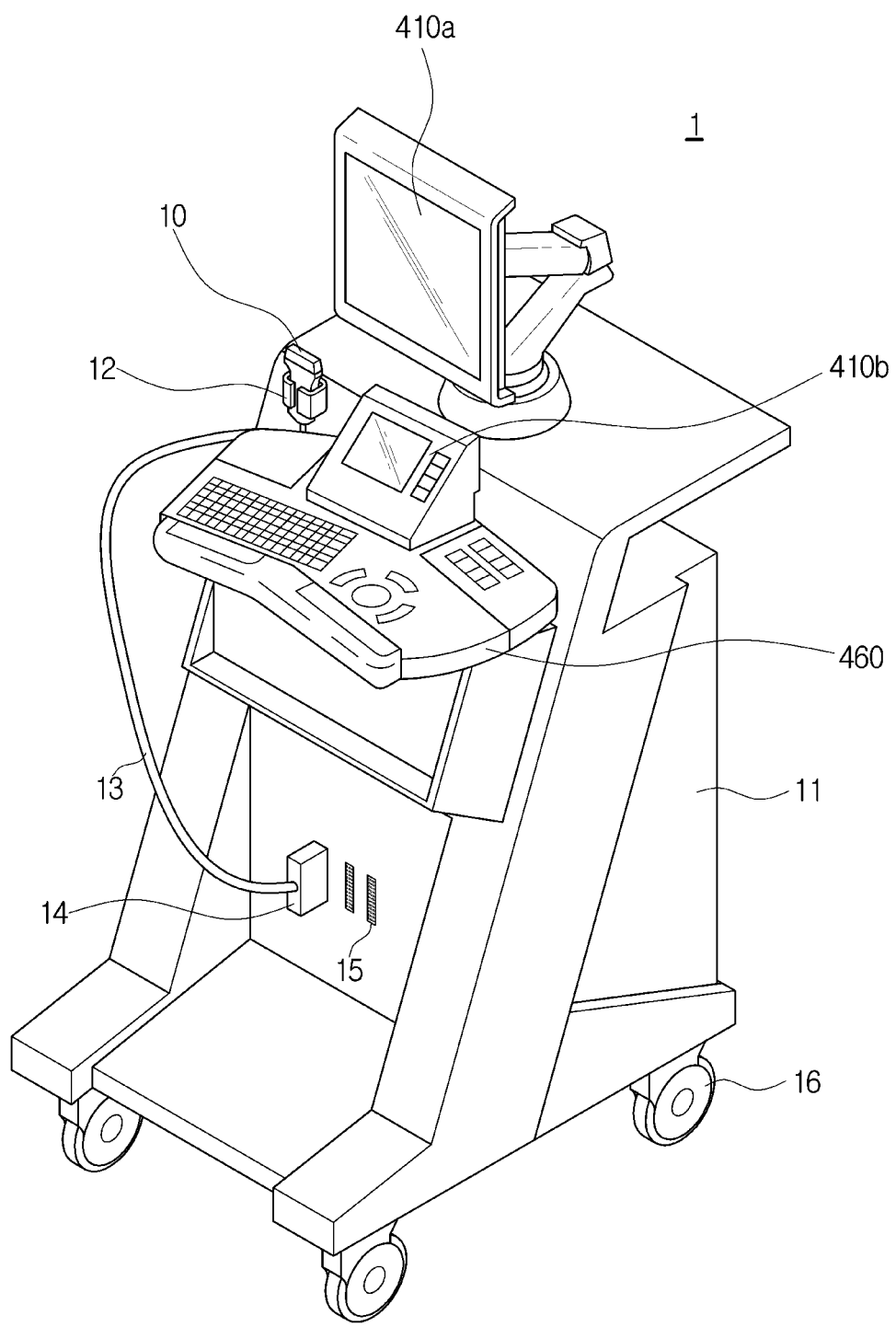
FIG. 1 is a perspective view illustrating an ultrasonic imaging apparatus according to an embodiment of the present invention.

Reference will now be made in detail to the embodiments of the present invention, examples of which are illustrated in the accompanying drawings, wherein like reference numerals refer to like elements throughout. In the following description of the present invention, a detailed description of known functions and configurations incorporated herein will be omitted when it may obscure the subject matter of the present invention.

The terms used in this specification have been selected in consideration of functions of corresponding constituents in the embodiments, and the definitions thereof may vary depending upon intention of a user or operator or practices. Therefore, the terms used in the embodiments described below should be construed as having meanings as commonly understood by those skilled in the art if not specifically defined. Terms specifically defined in this specification should be understood based on the definitions thereof in the specification.

In addition, unless specifically mentioned, aspects or constituents of embodiments selectively disclosed in this specification should be understood as being combinable with each other, although they are shown in the drawings as a single integrated configuration, so long as it is not apparent to those skilled in the art that they are contradictory to each other.

An ultrasonic imaging apparatus and a method for controlling the same according to embodiments of the present invention will hereinafter be described with reference to the attached drawings.

The ultrasonic imaging apparatus according to an embodiment will hereinafter be described with reference to FIGS. 1 and 2.

FIG. 1 is a perspective view illustrating an ultrasonic imaging apparatus according to an embodiment of the present invention.

Referring to FIG. 1, the ultrasonic imaging apparatus 1 may include a main body 11, an ultrasonic probe 10, an input unit 460, a sub-display 410a, and a main display 410b.

The main body 11 may receive a transmission (Tx) signal generator 112 of the ultrasonic imaging apparatus 1. If a user inputs an ultrasonic diagnostic command, the Tx signal generator 112 may generate a transmission (Tx) signal and transmit the Tx signal to the ultrasonic probe 10.

One or more female connectors 15 may be provided at one side of the main body 11. A male connector 14 coupled to a cable 13 may be physically coupled to the female connector 15. The Tx signal generated by the Tx signal generator may be transmitted to the ultrasonic probe 10 after passing through not only the male connector 14 coupled to the female connector 15 of the main body 11 but also the cable 13.

Meanwhile, a plurality of castors 16 for mobility of the ultrasonic imaging apparatus 1 may be located blow the main body 11. The plurality of castors 16 may fix the ultrasonic imaging apparatus 1 to a specific position, or may allow movement of the ultrasonic imaging apparatus 1 in a specific direction.

The ultrasonic probe 10 may contact the surface of a target object (ob) so as to transmit or receive ultrasonic waves. In more detail, the ultrasonic probe 10 may convert a signal received from the main body 11 into an ultrasonic signal, transmit the converted ultrasonic signal to the inside of the target object (ob), receive an ultrasonic echo signal reflected from a specific part contained in the target object (ob), and transmit the received ultrasonic echo signal to the main body 11.

For this purpose, a plurality of acoustic modules 7 for generating ultrasonic waves according to an electric signal may be provided at one end of the ultrasonic probe 10.

The acoustic module 7 may generate ultrasonic waves according to received AC (Alternating Current) power. In more detail, the acoustic module 7 may receive AC power from an external power-supply or an internal battery. A transducer of the acoustic module 7 vibrates according to the received AC power so as to generate ultrasonic waves.

The plurality of acoustic modules 7 may be implemented as a matrix array, a linear array, or a convex array. In addition, the plurality of acoustic modules 7 may be implemented as a phased array or a concave array. A cover for covering the acoustic modules may be arranged over the acoustic modules 7.

The cable 13 is coupled to the other end of the ultrasonic probe 10, and the male connector 14 may be coupled to the end of the cable 13. The male connector 14 may be physically coupled to the female connector 15 of the main body 11.

The input unit 460 may receive various input signals associated with the operations of the ultrasonic imaging apparatus 1 from a user. In addition, the input signals received through the input unit 460 may be supplied to the main body 11 by wire or wirelessly.

The input unit 460 may include at least one of a touchpad, a keyboard, a foot switch, and a foot pedal. The touchpad or keyboard may be implemented by hardware, and may be provided at an upper portion of the main body 11. The keyboard may include at least one of a switch, a key, a wheel, a joystick, a track ball, and a knob. In another example, the keyboard may also be implemented by software such as a graphical user interface (GUI). In this case, the keyboard may be displayed through the sub display 410a or the main display 410b. The foot switch or the foot pedal may be provided at a lower portion of the main body 11. A user (operator) may control the operation of the ultrasonic imaging apparatus 1 using the foot pedal.

The input signal received by the input unit 460 will hereinafter be described with reference to FIG. 2.

A probe holder 12 for holding the ultrasonic probe 10 may be disposed around the input unit 460. Therefore, a user may stow the ultrasonic probe 10 on the probe holder 12 when the ultrasonic imaging apparatus 1 is not used.

Although one probe holder 12 is disposed around the input unit 460 as shown in FIG. 1, the scope or spirit of the present invention is not limited thereto, the position or number of probe holders 12 may be modified in various ways according to the overall design of the ultrasonic imaging apparatus 1 or the design or position of some constituent elements of the ultrasonic imaging apparatus 1.

The display 410 may display images requisite for the user who manipulates the ultrasonic imaging apparatus 1 or the acquired ultrasonic images. In addition, the display 410 may include a sub display 410a and a main display 410b.

The sub display 410a may be provided in the main body 11. FIG. 1 exemplarily illustrates that the sub display 410a is disposed over the input unit 460. The sub display 410a may be implemented as a Cathode Ray Tube (CRT), a Liquid Crystal Display (LCD), etc. The sub display 410a may display a menu or information needed for ultrasonic diagnosis.

The main display 410b may be provided in the main body 11. FIG. 1 exemplarily illustrates that the main display 410b is disposed over the sub display 410a. The main display 410b may be implemented as a CRT or LCD. The main display 410b may display ultrasonic images acquired from an ultrasonic diagnostic process.

Although FIG. 1 exemplarily illustrates that both the sub display 410a and the main display 410b are contained in the ultrasonic imaging apparatus 1, it should be noted that the sub display 410a may be omitted as necessary. In this case, the application or menu displayed through the sub display 410a may also be displayed through the main display 410b as necessary.

In addition, at least one of the sub display 410a and the main display 410b may also be separated from the main body 11 as necessary.

Figure 2:
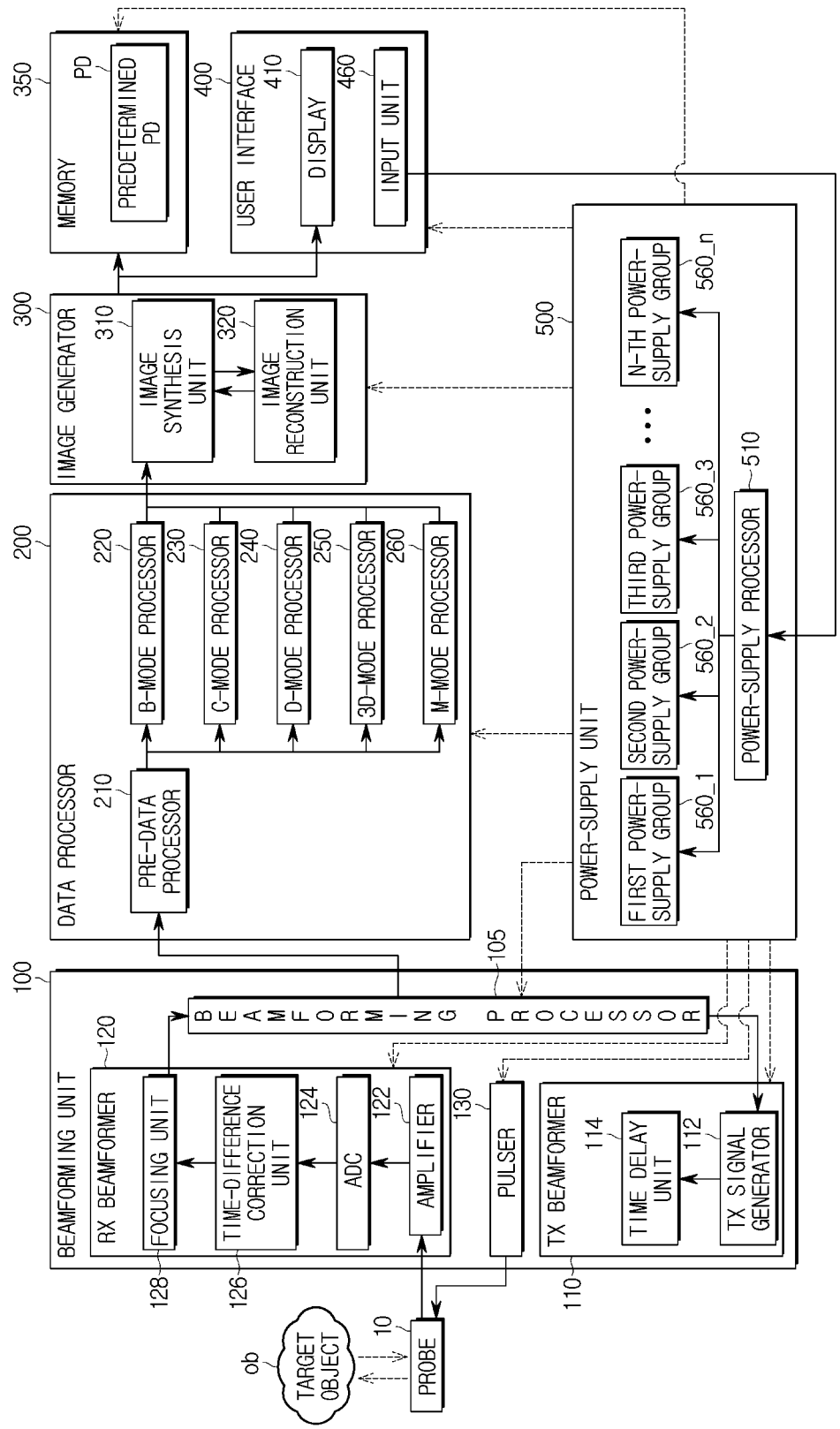
FIG. 2 is a block diagram illustrating an ultrasonic imaging apparatus according to an embodiment of the present invention.

FIG. 2 is a block diagram illustrating an ultrasonic imaging apparatus according to an embodiment of the present invention.

Referring to FIG. 2, the ultrasonic imaging apparatus 1 may include a probe 10, a beamforming unit 100, a data processor 200, an image generator 300, a memory 350, a user interface 400, and a power-supply unit 500.

The ultrasonic imaging apparatus 1 may be implemented as a cart-type or portable-type ultrasonic imaging apparatus. For example, the portable-type ultrasonic imaging apparatus may be implemented as any one of a picture archiving communication system (PACS) viewer, a smartphone, a laptop computer, a personal digital assistant (PDA), a tablet, a laptop computer, etc., without being limited thereto.

The probe 10 may output an ultrasonic signal to the target object (ob) upon receiving a drive signal from the beamforming unit 100, and receive an echo signal reflected from the target object (ob). The probe 10 may include a transducer, and the transducer may vibrate in response to the received electric signal, and generate ultrasonic waves corresponding to acoustic energy. In addition, the probe 10 may be coupled to the main body of the ultrasonic imaging apparatus 1 by wire or wirelessly, and the ultrasonic imaging apparatus 1 may include a plurality of probes 10 according to an implementation shape.

The beamforming unit 100 may transmit an ultrasonic signal to the target object (ob), and receive an echo ultrasonic signal reflected from the target object (ob). In more detail, the beamforming unit 100 may include a transmission (Tx) beamformer 110, a pulser 130, a reception (Rx) beamformer, and a beamforming processor 105.

The Tx beamformer 110 may output a drive signal to the probe 10, and may include a transmission (Tx) signal generator 112, and a time delay unit 114.

The Tx signal generator 112 may generate a pulse for forming a Tx ultrasonic signal according to a predetermined pulse repetition frequency (PRF). The time delay unit 114 may apply a delay time for deciding transmission directionality to the pulse. Individual pulses to which the delay time is applied may respectively correspond to a plurality of piezoelectric vibrators contained in the probe 10.

The pulser 130 may apply the drive signal (or driving pulse) to the probe 10 at different time points corresponding to respective pulses to which the delay time is applied.

The Rx beamformer 120 may process the echo signal received from the probe 10 so as to generate ultrasonic data, and may include an amplifier 122, an analog-to-digital converter (ADC) 124, a time-difference correction unit 126, and a focusing unit 128.

The amplifier 122 may amplify the echo signal per channel. The ADC 124 may perform analog-to-digital conversion (ADC) of the amplified echo signal, and thus output the digital echo signal. The time-difference correction unit 126 may apply the delay time for deciding reception directionality to the digital echo signal. The focusing unit 128 may sum echo signals processed by a reception (Rx) delay unit, and thus generate ultrasonic data.

Meanwhile, the Rx beamformer 120 may not include the amplifier 122 according to implementation format. That is, if sensitivity of the probe 10 increases or the number of processed bits increases, the amplifier 122 may be omitted as necessary.

The beamforming processor 105 may control the operation of the beamforming unit 100. In more detail, the beamforming processor 105 may control the Tx beamformer 110 so as to adjust a frequency, a magnitude, an irradiation direction, and depth of an ultrasonic signal to be generated from the probe 10. In addition, the beamforming processor 105 may arrange the position of the target object (ob) of a diagnostic part from which the corresponding signal is reflected according to the frequency, magnitude and Rx position of the received ultrasonic signal, and thus output the arranged result to the data processor 200.

The data processor 200 may analyze ultrasonic data received from the beamforming unit 100, and process the analyzed ultrasonic data in the form of a user-desired image.

In more detail, the data processor 200 may include a pre-data processor 210, a B-mode processor 220, a C-mode processor 230, a D-mode processor 240, a 3D-mode processor 250, and an M-mode processor 260.

The pre-data processor 210 may perform data processing before converting ultrasonic data into an ultrasonic image. In more detail, the pre-data processor 210 may perform sampling of ultrasonic data at intervals of a specific sampling time period. In addition, the pre-data processor 210 may detect the motion of a target part to be diagnosed by analyzing ultrasonic data, and may calculate a motion vector on the basis of the analyzed ultrasonic data.

In addition, the pre-data processor 210 may generate an ultrasonic image through scan conversion of the generated ultrasonic data, and display the generated ultrasonic image. Meanwhile, the ultrasonic image may include not only a gray-scale image and a three-dimensional (3D) image, that are obtained by scanning the target object (ob) in an amplitude (A) mode, a brightness (B) mode, and a motion (M) mode, but also a Doppler image for indicating a moving object (ob) using the Doppler effect. The Doppler image may include a blood-flow Doppler image (also called a color Doppler image) indicating blood flow, a tissue Doppler image indicating the movement of tissues, and a spectrum Doppler image for displaying the moving speed of the target object (ob) in a waveform format.

The B-mode processor may extract a B-mode component from ultrasonic data, and process the extracted B-mode component. The image generator 300 may generate an ultrasonic image in which signal strength is represented by brightness on the basis of the B-mode component extracted by the B-mode processor.

The C-mode processor may extract a C-mode component from ultrasonic data, and process the extracted C-mode component. The image processor 300 may generate ultrasonic images having different RGB ratios on the basis of the B-mode component extracted by the C-mode processor.

The D-mode processor may extract the Doppler component from ultrasonic data, and the image generator 300 may generate a Doppler image in which movement of the target object (ob) is represented by colors or waveforms on the basis of the extracted Doppler component.

The 3D-mode processor 250 may receive the output signals having different depths and different heights from the beamforming unit, analyze the received output signals to generate 3D volumes, and perform rendering of the 3D volumes by combining the 3D volumes.

The M-mode processor may analyze the time-variant movement of a specific diagnostic part of ultrasonic data, and generate an ultrasonic image on the basis of the analyzed result in such a manner that an ultrasonic image and a time axis can be simultaneously displayed.

The image generator 300 may temporally or spatially combine data processed by the data processor 200, and thus generate an ultrasonic image. In addition, the image generator 300 may include an image synthesis unit 310 and an image reconstruction unit 320.

The image synthesis unit 310 performs image registration of the sampled beamforming output signal that is temporally and spatially divided, temporally and spatially re-synthesizes the image registration result, and represents an ultrasonic image on the basis of the re-synthesized result.

In addition, the image reconstruction unit 320 may reconstruct the distorted ultrasonic image signal caused by a data processing step, a diagnostic step, or other reasons using an estimation function or an interpolation function.

In addition, the image generator 300 may also generate an elastic image for displaying the modification degree of the target object (ob) in response to pressure. Furthermore, the image generator 300 may also display various additional information (e.g., text or graphics) on the ultrasonic image. Meanwhile, the generated ultrasonic image may be stored in the memory 350.

The memory 350 may store various kinds of information processed by the ultrasonic imaging apparatus 1. For example, the memory 350 may store medical data associated with diagnosis of the target object (ob), for example, input/output ultrasonic data, an ultrasonic image, etc. The memory 350 may also store an algorithm or program executed by the ultrasonic imaging apparatus 1.

In addition, the memory 350 may store predetermined power data (PD) therein. In this case, the predetermined power data (PD) may be established when the ultrasonic imaging apparatus 1 is manufactured or designed according to a user input signal applied to the input unit 460. In more detail, the predetermined power data (PD) may be established in a manner that several power-supply groups 560 can adjust the magnitude and order of power-supply voltages to be applied to a plurality of elements contained in the ultrasonic imaging apparatus 1 according to a user-selected operation mode of the ultrasonic imaging apparatus 1. In addition, the predetermined power data (PD) may be established in a manner that several power-supply groups 560 can adjust the switching frequency and supply time of power-supply voltages to be applied to a plurality of elements contained in the ultrasonic imaging apparatus 1 according to a user-input transmission/reception (Tx/Rx) condition. The predetermined power data (PD) may include regulator information contained in the plurality of power-supply groups 560 so as to adjust the switching frequency.

The memory 350 may be implemented as various kinds of storage media, such as a flash memory 350, a hard disk drive (HDD), an EEPROM, etc. In addition, the ultrasonic imaging apparatus 1 may operate a web-based storage or cloud server configured to perform a storage function of the memory 350 over the Internet.

The user interface 400 may display a screen image through which the user can recognize the operation state of the ultrasonic imaging apparatus 1 and can input a desired command, and may receive a user input signal. In addition, the user interface 400 may include the input unit 460 and the display 410.

The input unit 460 may receive an input signal for the operation of the ultrasonic imaging apparatus 1 from the user.

In more detail, the input unit 460 may receive input signals associated with various operation modes, for example, an amplitude (A) mode, a brightness (B) mode, a color (C) mode, a Doppler (D) mode, a motion (M) mode, a 3D mode, etc. In addition, the input unit 460 may receive input signals associated with Tx/Rx information regarding the frequency and interval of transmission (Tx) ultrasonic signals, and may also receive input signals associated with Tx/Rx information regarding the frequency and intervals of reception (Rx) ultrasonic signals. In addition, the input unit 460 may receive an input signal associated with the beginning of ultrasonic diagnosis, and the like.

Categories of the input unit 460 may be identical to or different from those of the input unit 460 shown in FIG. 1. That is, although the input unit 460 may include hardware configurations, for example, a keypad, a mouse, a touch panel, a touchscreen, a track ball, a jog switch, etc., the scope or spirit of the present invention is not limited thereto, and the input unit 460 may further include various input units, for example, an electrocardiogram (ECG) measurement module, a respiratory measurement module, a voice recognition sensor, a gesture recognition sensor, a fingerprint recognition sensor, an iris recognition sensor, a depth sensor, a distance sensor, etc.

The display 410 may display and output the generated ultrasonic image. The display 410 may display not only the ultrasonic image but also various kinds of information processed by the ultrasonic imaging apparatus 1 on the screen through a Graphical User Interface (GUI). Meanwhile, the ultrasonic imaging apparatus 1 may include two or more displays 410 according to implementation formats.

The display 410 may include the sub display 410a and the main display 410b. The display 410, the sub display 410a, and the main display 410b may be identical to or different from those of FIG. 1.

The power-supply unit 500 can provide power-supply voltages for driving a plurality of elements contained in the ultrasonic imaging apparatus 1 on the basis of the input signal of the input unit 460. In addition, the power-supply unit 500 may convert DC power into AC power, and may also convert AC power into DC power. In addition, the power-supply unit 500 may include a plurality of power-supply groups 560 for respectively providing a plurality of elements with power-supply voltages, and a power-supply processor 510 for adjusting the power-supply voltages supplied from the plurality of power-supply groups 560.

The power-supply unit 500 will hereinafter be described with reference to FIGS. 4 and 5.

Figure 3:
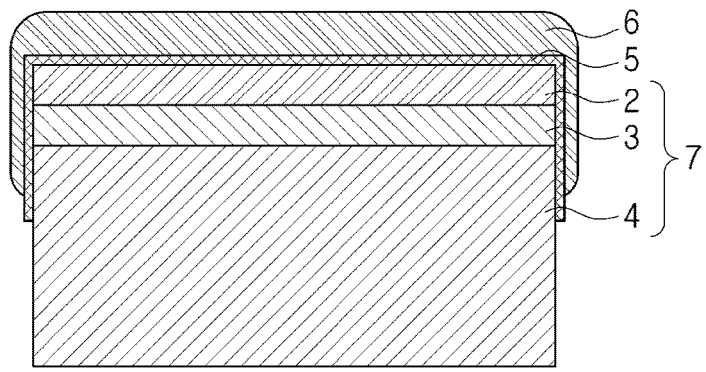
FIG. 3 is a cross-sectional view illustrating a piezoelectric layer according to an embodiment of the present invention.

FIG. 3 is a cross-sectional view illustrating a piezoelectric layer according to an embodiment of the present invention.

Referring to FIG. 3, the ultrasonic probe 10 may include an acoustic module 7, a protective layer 5, and a lens layer 6. The acoustic module 7 may include a piezoelectric layer 3, a backing layer 4 (serving as a sound absorption layer) provided at the bottom surface of the piezoelectric layer, and a matching layer 3 provided at the top surface of the piezoelectric layer 3. The protective layer 5 may cover the top surface of the acoustic module 7, and may partially cover a lateral surface of the acoustic module 7. The lens layer 6 may cover the top surface and lateral surface of the protective layer 5.

The acoustic module 100 may also be referred to as an ultrasonic transducer. Examples of the ultrasonic transducers may include a magnetostrictive ultrasonic transducer using magnetostrictive effects of a magnetic material, a capacitive micromachined ultrasonic transducer (cMUT) to transmit and receive ultrasonic waves using vibration of several hundred or thousand micromachined thin films, and a piezoelectric ultrasonic transducer using piezoelectric effects of a piezoelectric material. Hereinafter, a piezoelectric ultrasonic transducer will be described as one embodiment of the transducer.

When mechanical pressure is applied to a certain material, voltage is generated, and when voltage is applied, mechanical deformation occurs. Such an effect is referred to as the piezoelectric effect or the inverse piezoelectric effect, and a material having such an effect is referred to as a piezoelectric material. That is, a piezoelectric material is a material which converts electric energy into mechanical vibration energy and vice versa.

The ultrasonic probe 10 may include the piezoelectric layer 3 which receives electrical signals and converts the electrical signals into mechanical vibration so as to generate ultrasonic waves.

The piezoelectric material constructing the piezoelectric layer 3 may include a PZT (lead zirconate titanate) ceramic, a PZMT single crystal made of a solid solution of lead magnesium niobate and lead titanate, a PZNT single crystal made of a solid solution of lead zinc niobate and lead titanate, or the like. In addition, various other materials for converting electric signals into mechanical vibration may also be used as an example of the piezoelectric material constructing the piezoelectric layer 3.

In addition, the piezoelectric layer 3 may be arranged in a single-layer or in a stack of multiple layers. Generally, the piezoelectric layer 3 in the form of a stack may be more advantageous in terms of impedance and voltage adjustment, thus achieving high energy conversion efficiency and tender spectrums. In addition, various other structures in consideration of the performance of the piezoelectric layer 3 may be used as one example of the structure of the piezoelectric layer 3.

The backing layer (serving as a sound absorption layer) 4 may be installed to the lower surface of the piezoelectric layer 3 to absorb ultrasonic waves generated in and moving rearward of the piezoelectric layer 3, thereby preventing ultrasonic waves from moving rearward of the piezoelectric layer 3. Consequently, the backing layer 4 may prevent image distortion. The backing layer 4 may be formed in multiple layers to increase attenuation or prevention of ultrasonic waves. In addition, various structures to increase attenuation or prevention of ultrasonic waves may be used as one example of the structure of the backing layer 4.

The matching layer 2 may be installed at the upper surface of the piezoelectric layer 3. The matching layer 2 may reduce a difference in acoustic impedances between the piezoelectric layer 3 and a target object (ob) to match the acoustic impedances of the piezoelectric layer 3 and the target object (ob) with each other, thereby allowing ultrasonic waves generated in the piezoelectric layer 3 to be efficiently transmitted to the target object (ob). To this end, the impedance of the matching layer 2 may have a median value between the acoustic impedance of the piezoelectric layer 3 and the acoustic impedance of the target object (ob).

The matching layer 2 may be formed of glass or a resin. In addition, various other materials to match the acoustic impedances of the piezoelectric layer 3 and the target object (ob) with each other may be used as one example of a constituent material of the matching layer 2.

In addition, the matching layer 2 may include a plurality of matching layers 2 to ensure stepwise variation of acoustic impedance from the piezoelectric layer 3 to the target object (ob), and the matching layers 2 may be formed of different materials. Additionally, various other structures to ensure stepwise variation of acoustic impedance may be used as one example of the structure of the matching layer 2.

The piezoelectric layer 3 and the matching layer 2 may be processed into a 2-dimensional (2D) matrix array by dicing, or may be processed into a 1D matrix array.

The protective layer 5 may be installed to cover an upper surface of the matching layer 2 and a portion of the side surface of the acoustic module 7. The protective layer 5 may include a chemical shield to protect internal elements from water and medicines used for disinfection. The chemical shield may be formed by coating or depositing a conductive material on a surface of a moisture-proof and chemical-resistant film. For example, the chemical shield may be formed by implementing Parylene coating of a polymer film on the upper surface of the matching layer 2 and a portion of the side surface of the acoustic module 7. In another example, the chemical shield may be formed by sputtering a surface of a polymer film.

In addition, the protective layer 5 may include a Radio Frequency (RF) shield to prevent leakage of RF waves from the piezoelectric layer 3 as well as introduction of an external RF signal. Naturally, various other configurations to prevent introduction/leakage of RF components may be used as one example of a constituent configuration of the protective layer 5.

The lens layer 6 may be installed to cover the upper surface and the side surface of the protective layer 5. The lens layer 6 may be formed of a low-attenuation material to prevent attenuation of an ultrasonic signal generated in the piezoelectric layer 3. For example, the lens layer 6 may be formed of a low viscosity epoxy resin, such as DER322 or DEH24. In addition, various other materials to prevent attenuation of an ultrasonic signal may be used as one example of a constituent material of the lens layer 6. As a result of forming the lens layer 6 of a low-attenuation material, it may be possible to enhance ultrasonic signal sensitivity.

Moreover, as a result of installing the lens layer 6 to cover a portion of the side surface of the acoustic module 7, i.e. a portion of the outer surface of the acoustic module 7, it may be possible to reduce crosstalk.

The power-supply unit, a plurality of internal components of the power-supply unit, and a user interface contained in the ultrasonic imaging apparatus according to embodiments of the present invention will hereinafter be described with reference to FIGS. 4 and 5.

Figure 4:
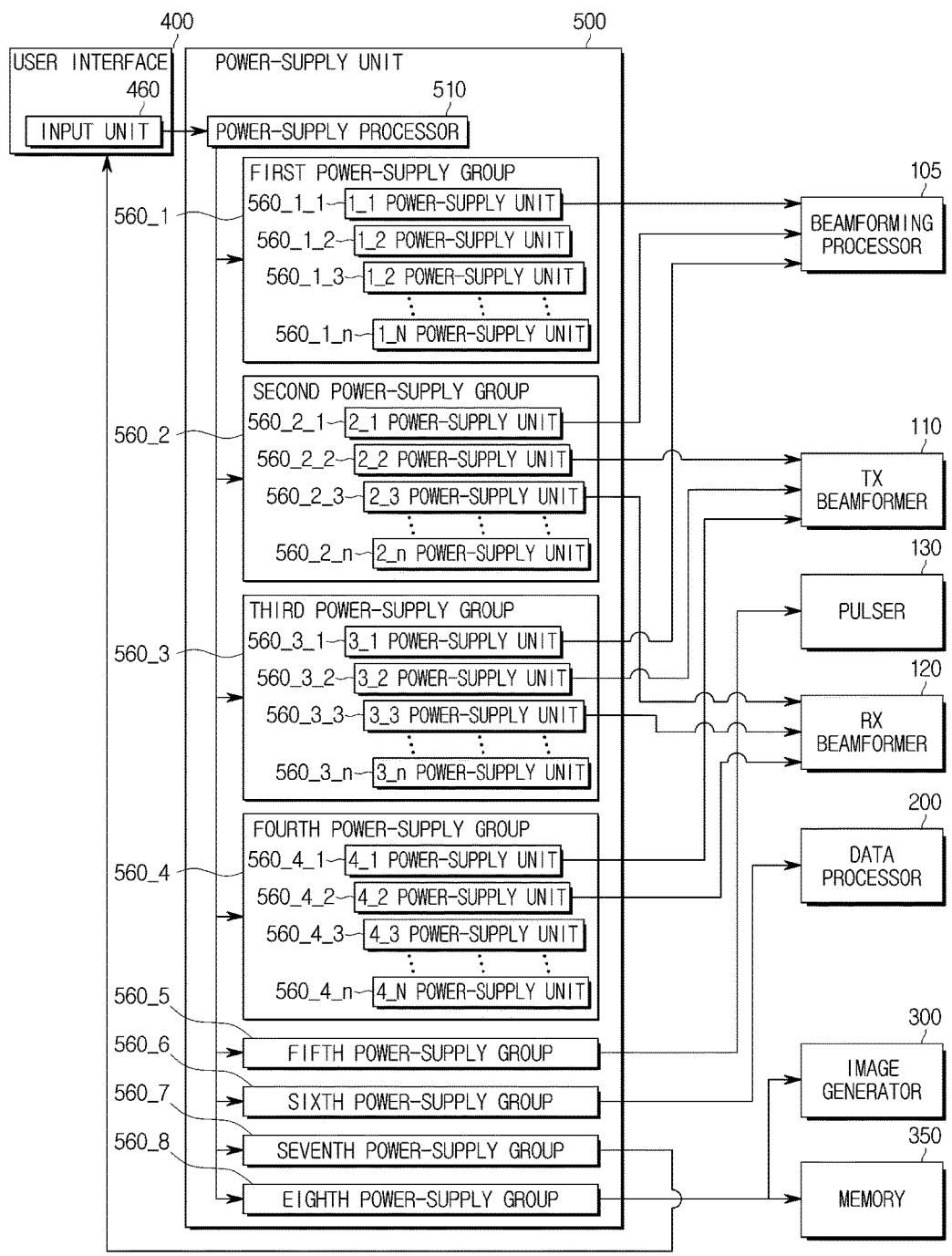
FIG. 4 is a block diagram illustrating a power-supply unit for supplying a power-supply voltage to a plurality of elements according to an embodiment.

FIG. 4 is a block diagram illustrating a power-supply unit for supplying a power-supply voltage to a plurality of elements according to an embodiment.

Referring to FIG. 4, the ultrasonic imaging apparatus 1 may include a beamforming processor 105, a transmission (Tx) beamformer 110, a pulser 130, a reception (Rx) beamformer 12, a data processor 200, an image generator 300, a user interface 400, and a power-supply unit 500.

The beamforming processor 105, the Tx beamformer 100, the pulser 130, the Rx beamformer 120, the data processor 200, the image generator 300, and the memory 350 shown in FIG. 4 may be identical to or different from the beamforming processor 105, the Tx beamformer 110, the pulser 130, the Rx beamformer 120, the data processor 200, the image generator 300, and the memory 350 shown in FIG. 2.

The user interface 400 may include the input unit 360 for receiving an input signal regarding a user-desired operation. The user may input the operation mode of the ultrasonic imaging apparatus 1 through the input unit 460.

In more detail, the user who uses the input unit 460 may select whether an ultrasonic image to be obtained or displayed through the ultrasonic imaging apparatus 1 is a brightness (B) mode, a color Doppler (CD) mode, or a spectral Doppler mode image. If the user selects the spectral Doppler mode, the user may also select whether the spectral Doppler mode is a pulsed wave (PW) mode or a continuous wave (CW) mode using the input unit 460.

The power-supply unit 500 may output power-supply voltages to a plurality of elements contained in the ultrasonic imaging apparatus 1.

In more detail, the power-supply unit 500 may select a power-supply group 560 scheduled to power on a plurality of elements on the basis of a user input signal received by the input unit 460, and may supply or adjust power-supply voltages to be applied to the plurality of elements.

In addition, the power-supply unit 500 may include a power-supply processor 510 and a power-supply group 560.

The power-supply processor 510 may receive the input signal entered through the input unit 460, and may retrieve predetermined power data (PD) stored in the memory 350. In addition, the power-supply processor 510 may search for power data (PD) corresponding to the received input signal from among predetermined power data (PD) retrieved from the memory 350, and may determine a power-supply signal to be adjusted according to the searched power data (PD). In addition, the power-supply processor 510 may output a control signal to a plurality of power-supply groups 560 configured to adjust power-supply voltages.

For example, the power-supply processor 510 may search for predetermined power data (PD) according to the CD mode from among the predetermined power data (PD) when the input signal received from the input unit 460 is a Color Doppler (CD) mode signal. A control signal is applied to a plurality of power-supply groups 560 according to the searched PD, such that power-supply voltages to be applied to the plurality of elements can be adjusted. That is, the magnitude and power of voltages applied to the plurality of elements and the power applied to the plurality of elements can be adjusted.

As a result, different power levels may be required for the plurality of elements contained in the ultrasonic imaging apparatus 1 according to individual modes, such that power can be optimized for respective user-selected modes.

The power-supply group 560 may include a plurality of power-supply groups 560 capable of being distinguished and driven independently of each other.

The plurality of power-supply groups 560 may output different voltages. For example, the power-supply group 560 may include a first power-supply group (560_1), a second power-supply group (560_2), a third power-supply group (560_3), a fourth power-supply group (560_4), a fifth power-supply group (560_5), a sixth power-supply group (560_6), and a seventh power-supply group (560_7). In addition, the first power-supply group (560_1) may output a voltage of 1.8V, and the first power-supply group (560_1) may include a plurality of power-supply groups (560_1_1 to 560_1_$n$). In addition, the second power-supply group (560_2) may output a voltage of 3.3V, and the second power-supply group (560_2) may include a plurality of power-supply groups (560_2_1 to 560_2_$n$). A third power-supply group (560_3) may output a voltage of 5V, and the third power-supply group (560_3) may include a plurality of power-supply groups (560_3_1 to 560_3_$n$). A fourth power-supply group (560_4) may output a voltage of 12V, and the fourth power-supply group (560_4) may include a plurality of power-supply groups (560_4_1 to 560_4_$n$). In addition, a fifth power-supply group (560_5) may output power-supply voltages of 1V to 100V so as to generate the operation signal.

In addition, the beamforming processor 105 may receive power-supply signals from the 1_1-th power-supply unit (560_1_1), the 2_1-th power-supply unit (560_2_1), and the 3_1-th power-supply unit (560_3_1). The Tx beamformer 110 may receive power-supply signals from the 2_2-th power-supply unit (560_2_2), the 3_2-th power-supply unit (560_3_2), and the 4_1-th power-supply unit (560_4_1). The pulser 130 may receive a power-supply signal from the fifth power-supply group (560_5), and the Rx beamformer 120 may receive power-supply signals from the 2_3-th power-supply unit (560_2_3), the 3_3-th power-supply unit (560_3_3), and the 4_2-th power-supply unit (560_4_2). In addition, the data processor 200 may receive a power-supply signal from the $6^{th}$ power-supply group (560_6), the user interface 400 may receive a power-supply signal from the $7^{th}$ power-supply group (560_7), and the image generator 300 and the memory 350 may receive a power-supply signal from the $8^{th}$ power-supply group (560_8).

Figure 5:
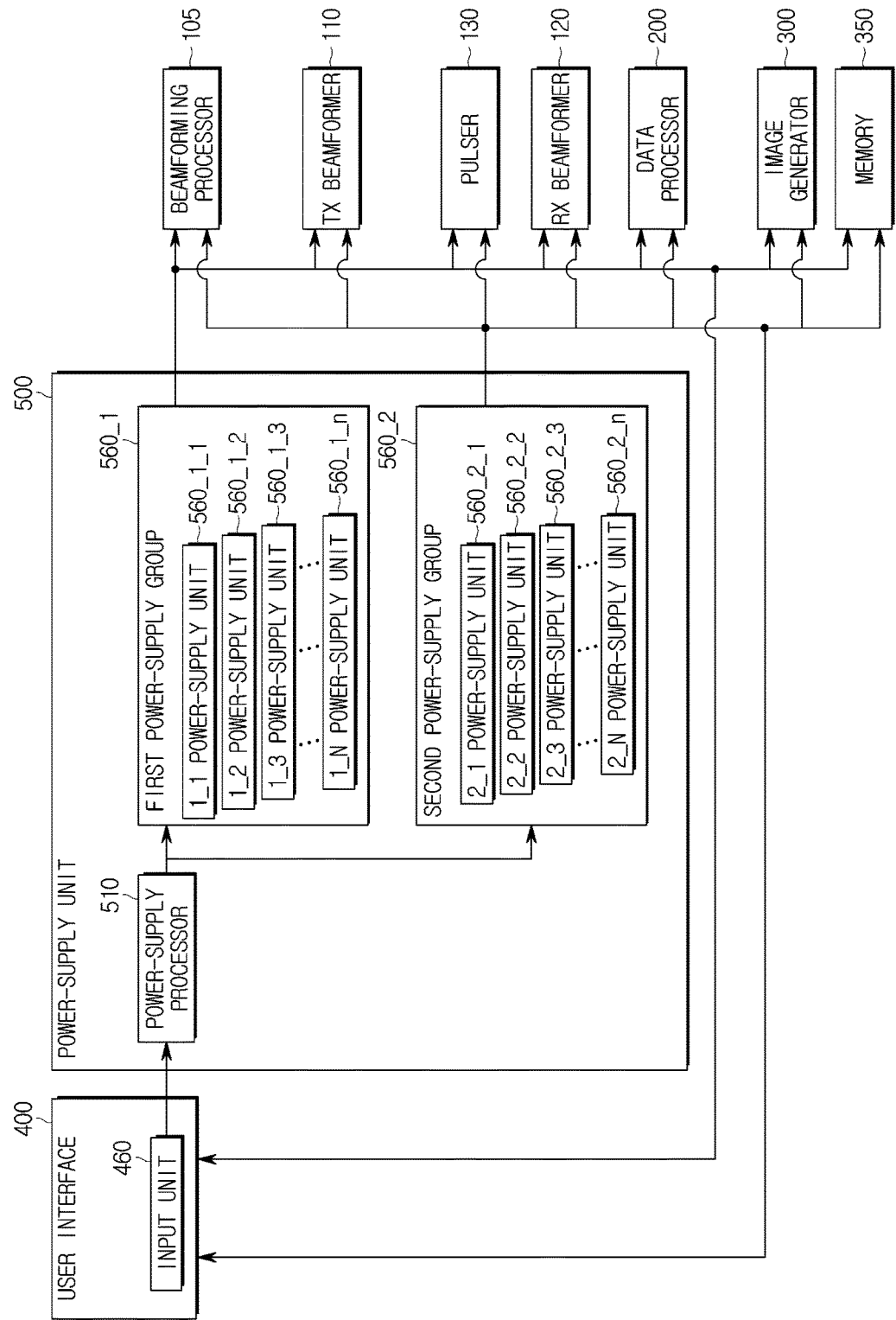
FIG. 5 is a block diagram illustrating a concept of supplying a power-supply voltage to a plurality of elements according to another embodiment.

FIG. 5 is a block diagram illustrating a concept of supplying a power-supply voltage to a plurality of elements according to another embodiment.

Referring to FIG. 5, the ultrasonic imaging apparatus 1 may include a beamforming processor 105, a Tx beamformer 110, a pulser 130, an Rx beamformer 120, a data processor 200, an image generator 300, a memory 350, a user interface 400, and a power-supply unit 500.

The beamforming processor 105, the Tx beamformer 110, the pulser 130, the Rx beamformer 120, the data processor 200, the image generator 300, and the memory 350 shown in FIG. 5 may be identical to or different from the beamforming processor 105, the Tx beamformer 110, the pulser 130, the Rx beamformer 120, the data processor 200, the image generator 300, and the memory 350 shown in FIG. 2.

The user interface 400 may include the input unit 460 for receiving an input signal regarding a user-desired operation. The user may input Tx/Rx conditions of the ultrasonic imaging apparatus 1 through the input unit 460.

In more detail, the user who uses the input unit 460 may select the frequency and interval of ultrasonic waves to be transmitted through the ultrasonic probe 10, and may select the frequency and interval of echo ultrasonic waves to be reflected from the target object (ob). For example, the user may select that the frequency of Tx/Rx ultrasonic waves is 2 MHz.

The power-supply unit 500 may provide power-supply signals to a plurality of elements contained in the ultrasonic imaging apparatus 1.

In more detail, the power-supply unit 500 may select a power-supply group 560 scheduled to power on the plurality of elements on the basis of the user input signal received by the input unit 460, and may provide and adjust power-supply signals to be applied to the plurality of elements.

In addition, the power-supply unit 500 may include a power-supply processor 510 and a power-supply group 560.

The power-supply processor 510 may receive the input signal entered through the input unit 460, and may retrieve predetermined power data (PD) stored in the memory 350. In addition, the power-supply processor 510 may search for power data (PD) corresponding to the received input signal from among the predetermined power data (PD) retrieved from the memory 350, and may determine a power-supply signal to be adjusted according to the searched power data (PD). In addition, the power-supply processor 510 may transmit a control signal to a plurality of power-supply groups 560 so as to perform power adjustment.

For example, the power-supply processor 510 may be greatly affected by noise if the input signal received from the input unit 460 is a continuous wave (CW) mode signal, so that a power-supply signal is supplied to a power-supply group 560 less affected by noise, resulting in reduction of noise. Therefore, the power-supply processor 510 may search for predetermined power data (PD) according to the CW mode from among the predetermined power data (PD), transmit a control signal to a plurality of power groups 560 according to the searched PD, and thus adjust a power-supply signal to be applied to a plurality of elements. That is, the switching frequency and the supply time point of voltage signals supplied to individual elements can be adjusted.

As a result, deterioration in the image quality of the ultrasonic image is prevented because the switching frequency of the power-supply unit 500 affects Tx/Rx ultrasonic waves through compensation interference or destructive interference.

The power-supply group 560 may include a plurality of power-supply groups 560 capable of being distinguished and driven independently of each other.

The plurality of power-supply groups 560 may output different voltages. For example, the power-supply group 560 may include a first power-supply group (560_1) and a second power-supply group (560_2). In addition, the first power-supply group (560_1) may include a switching regulator that is greatly affected by noise and has high efficiency. The first power-supply group (560_1) may include a plurality of power-supply groups (560_1_1 to 560_1_n). In addition, the second power-supply group (560_2) may include a linear regulator less affected by noise but having low efficiency, and the second power-supply group (560_2) may include a plurality of power-supply units (560_2_1 to 560_2_n).

Figure 6:
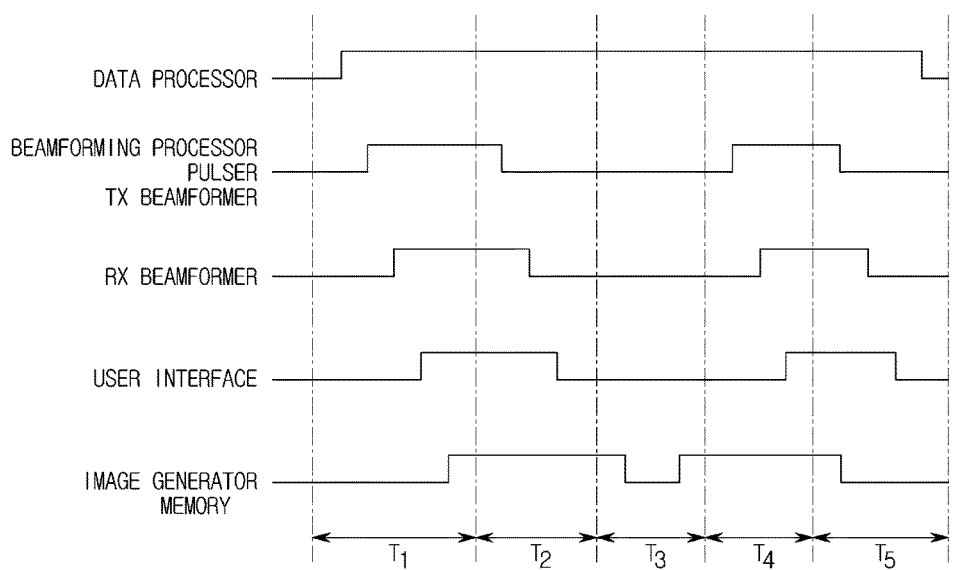
FIG. 6 is a graph illustrating power-supply voltages supplied from a power-supply unit to a plurality of elements according to different orders according to an embodiment.

FIG. 6 is a graph illustrating power-supply voltages supplied from a power-supply unit to a plurality of elements according to different orders according to an embodiment.

If the user inputs a desired operation mode through the input unit 460, the ultrasonic imaging apparatus 1 may be time-serially driven in the order of a start section T1, a stop section T2, an other-construction start section T3, a driving section T4, and a termination section T5.

In this case, the power-supply unit 500 may retrieve predetermined power data (PD) stored in the memory 350, search for PD corresponding to the operation mode received by the input unit 460 from among the predetermined PD, determine the searched PD, provide a power-supply signal to each element contained in the ultrasonic imaging apparatus 1 according to the PD, and adjust the power-supply signal.

In more detail, the power-supply unit 500 may provide a power-supply signal to the data processor during the start section T1, and then power on the beamforming processor 105, the pulser 130, and the Tx beamformer 110. Thereafter, the power-supply unit 500 may sequentially power on the Rx beamformer 120 and the user interface 400 during the start section T1, and then power on the image generator 300 and the memory 350.

In addition, during the stop section T2, the power-supply unit 500 may continuously power on the data processor, the image generator 300, and the memory 350, may power off the beamforming processor 105, the pulser 130, and the Tx beamformer 110, and may finally power off the Rx beamformer 120. Thereafter, the power-supply unit 500 may power off the user interface 400 during the stop section T2.

During the other-construction start section T3, the power-supply unit 500 may continuously power on the data processor, and may continuously power off the beamforming processor 105, the pulser 130, the Tx beamformer 110, the Rx beamformer 120, and the user interface 400. In addition, during the other-construction start section T3, the power-supply unit 500 may power off the image generator 300 and the memory 350, and may then power on the image generator 300 and the memory 350.

During the driving section T4, the power-supply unit 500 may continuously power on the data processor, the image generator 300, and the memory 350, and may power on the beamforming processor 105, the pulser 130, and the Tx beamformer 110. Thereafter, the power-supply unit 500 may sequentially power on the Rx beamformer 120 and the user interface 400 during the driving section T4.

During the termination section T5, the power-supply unit 500 may power off the beamforming processor 105, the pulser 130, the Tx beamformer 110, the image generator 300, and the memory 350, and may then power off the Rx beamformer 120. Thereafter, during the termination section T5, the power-supply unit 500 may power off the user interface 400, and may then power off the data processor.

Constituent elements of the ultrasonic imaging apparatus have been described above. A method for allowing the power-supply unit to power on a plurality of elements according to the embodiments will hereinafter be described with reference to FIGS. 7 and 8.

Figure 7:
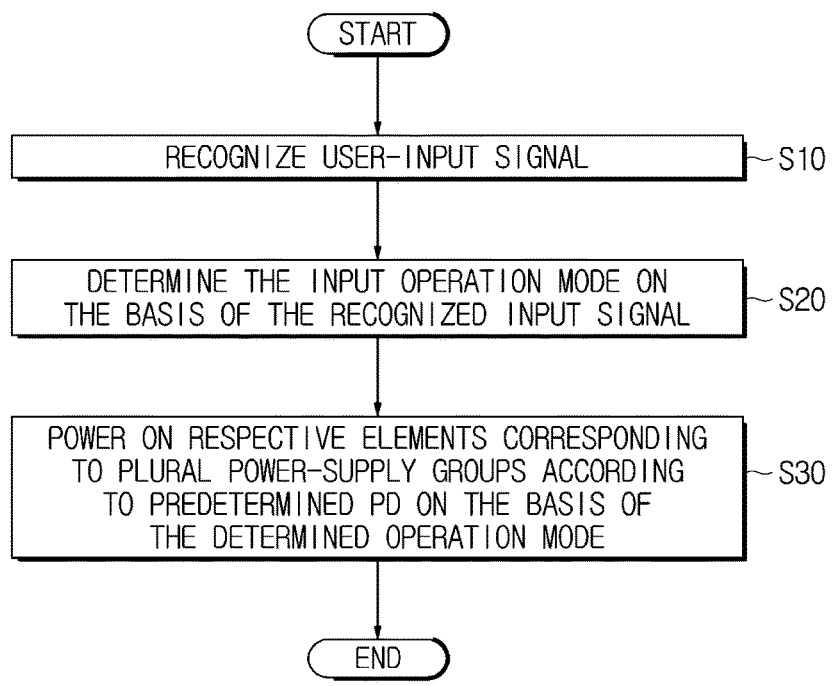
FIG. 7 is a flowchart illustrating a method for allowing a power-supply unit to provide a plurality of elements with power-supply voltages according to an embodiment.

FIG. 7 is a flowchart illustrating a method for allowing a power-supply unit to provide a plurality of elements with power-supply voltages according to an embodiment.

Referring to FIG. 7, the input unit may recognize an input signal entered by the user, and transmit the recognized input signal to the power-supply processor in operation S10. The power-supply processor may determine which operation mode of the ultrasonic imaging apparatus is selected by the input signal recognized on the basis of the input signal of the input unit in operation S20.

In addition, the power-supply processor may search for power data (PD) corresponding to the input operation mode from among predetermined power data (PD) on the basis of the operation mode applied to the ultrasonic imaging apparatus, and may power on a plurality of elements corresponding to a plurality of power-supply groups according to the retrieved power data (PD) in operation S30.

FIG. 8 is a flowchart illustrating a method for allowing a power-supply unit to provide a plurality of elements with power-supply voltages according to another embodiment.

Referring to FIG. 8, the input unit may recognize the input signal entered by the user, and may transmit the user input signal to the power-supply processor in operation S110. The power-supply processor may determine Tx/Rx conditions associated with the frequency and interval of ultrasonic waves to be transmitted and received in the ultrasonic imaging apparatus on the basis of the input signal recognized by the input signal in operation S120.

In addition, the power-supply processor may search for power data (PD) corresponding to input Tx/Rx conditions from among predetermined power data (PD) on the basis of Tx/Rx conditions applied to the ultrasonic imaging apparatus, and may power on a plurality of elements corresponding to a plurality of power-supply groups according to the searched power data (PD) in operation S130.

As is apparent from the above description, the ultrasonic imaging apparatus and the method for controlling the same according to the embodiments can allow a plurality of power-supply groups to adjust power-supply voltages respectively applied to a plurality of elements, resulting in increased power efficiency and reduced signal distortion.

The above-mentioned embodiments are disclosed only for illustrative purposes. The above-mentioned disclosures are used only to indicate the embodiments, and the present invention can also be used in various combinations, modifications and environments without departing from the scope or spirit of the present invention. That is, the present invention can be readily modified or changed within the scope of the present invention, within the scope equivalent to the disclosed content, and/or within the scope of technology or knowledge well known to those skilled in the art. The above-mentioned embodiments have exemplarily described the best mode for implementing a technical idea of the present invention, and various modifications needed for detailed application fields and utilities can also be made available. Therefore, the above-mentioned embodiments are exemplary and explanatory and are not intended to limit the scope of the present invention. In addition, the appended claims may conceptually include other embodiments or examples without departing from the scope or spirit of the present invention as necessary.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic imaging apparatus comprising:
   a user interface configured to receive an input signal of a user; and
   a power-supply unit including:
      a first power-supply group including a first regulator and configured to provide first power-supply signals for respectively driving first and second elements; and
      a second power-supply group including a second regulator and configured to provide second power-supply signals for respectively driving the first and second elements,
   wherein the power-supply unit searches for first power data corresponding to the received input signal from among predetermined power data and adjusts the first and second power-supply signals applied to respective first and second elements corresponding to the first and second power-supply groups according to the first power data by turning on or off at least one of the first power-supply group or the second power-supply group,
   wherein the input signal indicates transmission/reception (Tx/Rx) conditions determining a frequency and an interval of ultrasonic waves to be transmitted and received,
   wherein the power-supply unit searches for second power data corresponding to the transmission/reception (Tx/Rx) conditions from among the predetermined power data, and adjusts a switching frequency and a supply time point of the first and second power-supply signals respectively applied to the first and second elements according to the second power data; and
   wherein the predetermined power data includes information of the first and second regulators contained in the first and second power-supply groups, respectively, to adjust the switching frequency.

2. The ultrasonic imaging apparatus according to claim 1, wherein the power-supply unit adjusts magnitudes of the first and second power-supply signals respectively applied to the first and second elements.

3. The ultrasonic imaging apparatus according to claim 1, wherein the input signal is an operation mode of the ultrasonic imaging apparatus, and
   wherein the power-supply unit searches for third power data corresponding to the input operation mode, and adjusts supply time points of the first and second power-supply signals respectively applied to the first and second elements according to the third power data.

4. The ultrasonic imaging apparatus according to claim 1, wherein the first and second regulators are different from each other.

5. The ultrasonic imaging apparatus according to claim 1, wherein the first and second power-supply groups are coupled in parallel according to the same-magnitude voltages.

6. A method for controlling an ultrasonic imaging apparatus, comprising:
   receiving an input signal of a user;
   searching for power data corresponding to the input signal from among predetermined power data; and
   adjusting power-supply signals applied to first and second elements corresponding to first and second power-supply groups, respectively, according to the power data by turning on or off at least one of the first power-supply group or the second power-supply group,
   wherein the input signal indicates transmission/reception (Tx/Rx) conditions determining a frequency and an interval of ultrasonic waves to be transmitted and received,
   wherein the adjusting of the power-supply signals includes adjusting a switching frequency and a supply time point of the power-supply signals respectively applied to the first and second elements according to the power data, and
   wherein the predetermined power data includes information of regulators contained in the first and second power-supply groups, respectively, to adjust the switching frequency.

7. The method according to claim 6, wherein the adjusting of the power-supply signals includes adjusting magnitudes of the power-supply signals applied to the first and second elements, respectively.

8. The method according to claim 6, wherein the input signal is an operation mode of the ultrasonic imaging apparatus, and
   wherein the adjusting of the power-supply signals includes adjusting supply time points of the power-supply signals respectively applied to the first and second elements.

9. The method according to claim 8, wherein the adjusting of the supply time points of the power-supply signals includes adjusting orders of power-supply signals applied to the first and second elements, respectively.

10. The method according to claim 6, wherein the adjusting of the switching frequency includes turning on or off at least one of the first power-supply group or the second power-supply group respectively having different regulators.

11. The method according to claim 6, wherein the first and second power-supply groups are coupled in parallel according to the same-magnitude voltages.

\* \* \* \* \*